US008272870B2

(12) United States Patent
Van Lierde et al.

(10) Patent No.: US 8,272,870 B2
(45) Date of Patent: Sep. 25, 2012

(54) DEVICE FOR SECURING A DENTAL ATTACHMENT TO AN IMPLANT

(75) Inventors: Carl Van Lierde, Meerbeke (BE); Alessio Esposti, Watermael-Boitsfort (BE)

(73) Assignee: Materialise Dental N.V., Leuven (BE)

( * ) Notice: Subject to any disclaimer, the term of this patent is extended or adjusted under 35 U.S.C. 154(b) by 369 days.

(21) Appl. No.: 12/513,320

(22) PCT Filed: Nov. 3, 2006

(86) PCT No.: PCT/EP2006/010557
§ 371 (c)(1),
(2), (4) Date: May 1, 2009

(87) PCT Pub. No.: WO2008/052586
PCT Pub. Date: May 8, 2008

(65) Prior Publication Data
US 2010/0055640 A1 Mar. 4, 2010

(51) Int. Cl.
*A61C 19/04* (2006.01)
(52) U.S. Cl. .......................................... 433/72; 433/172
(58) Field of Classification Search ............... 433/72–76, 433/172–177, 167, 168.1, 193, 194, 199.1; 411/439–499; 24/713.6
See application file for complete search history.

(56) References Cited

U.S. PATENT DOCUMENTS

| | | | | |
|---|---|---|---|---|
| 4,362,511 A | * | 12/1982 | Jacklich | 433/220 |
| 4,431,416 A | * | 2/1984 | Niznick | 433/174 |
| 4,631,031 A | * | 12/1986 | Richter | 433/173 |
| 4,746,293 A | * | 5/1988 | Lundgren et al. | 433/173 |
| 4,756,689 A | * | 7/1988 | Lundgren et al. | 433/173 |
| 4,761,860 A | * | 8/1988 | Krauss | 24/713.6 |
| 4,832,601 A | * | 5/1989 | Linden | 433/173 |
| 4,906,191 A | * | 3/1990 | Soderberg | 433/213 |
| 4,981,735 A | * | 1/1991 | Rickson | 428/36.9 |

(Continued)

FOREIGN PATENT DOCUMENTS

AT 375012 6/1984

(Continued)

OTHER PUBLICATIONS

Office Action issued by Japan Patent Office (JPO) for Japanese Patent Application No. 534988/2009, dated Nov. 1, 2011 (6 pages).

*Primary Examiner* — Cris L Rodriguez
*Assistant Examiner* — Matthew Saunders
(74) *Attorney, Agent, or Firm* — Bacon & Thomas, PLLC

(57) ABSTRACT

An anchorage unit fits to a dental implant. A dental attachment for mounting to the anchorage unit has a first attachment part and a second attachment part. The attachment parts define an aperture for accommodating a portion of the anchorage unit with a boundary wall of the aperture on each of the attachment parts serving, in use, as a jaw for clamping against the portion of the anchorage unit. The aperture is of greater size than the portion of the anchorage unit to allow adjustment of the position of the attachment with respect to the anchorage unit. In another embodiment, a two-part anchoring assembly defines a pair of jaws for, in use, receiving and clamping against a portion of a dental attachment. The apparatus is particularly relevant when an attachment must be placed on more than one implant simultaneously.

26 Claims, 9 Drawing Sheets

U.S. PATENT DOCUMENTS

| | | | | |
|---|---|---|---|---|
| 4,986,753 A * | 1/1991 | Sellers | | 433/172 |
| 5,015,186 A * | 5/1991 | Detsch | | 433/173 |
| 5,116,225 A * | 5/1992 | Riera | | 433/173 |
| 5,195,891 A * | 3/1993 | Sulc | | 433/173 |
| 5,221,206 A * | 6/1993 | Nardi | | 433/193 |
| 5,320,529 A * | 6/1994 | Pompa | | 433/76 |
| 5,344,457 A * | 9/1994 | Pilliar et al. | | 606/60 |
| 5,421,722 A * | 6/1995 | Stemmann | | 433/189 |
| 5,816,810 A * | 10/1998 | Antonson et al. | | 433/173 |
| 5,871,357 A * | 2/1999 | Tseng | | 433/189 |
| 5,885,078 A * | 3/1999 | Cagna et al. | | 433/172 |
| 5,890,902 A * | 4/1999 | Sapian | | 433/173 |
| 5,975,902 A * | 11/1999 | Emmanuel | | 433/173 |
| 5,997,299 A * | 12/1999 | Unger | | 433/173 |
| 6,099,527 A * | 8/2000 | Hochschuler et al. | | 606/279 |
| 6,190,169 B1 * | 2/2001 | Bluemli et al. | | 433/172 |
| 6,305,938 B1 * | 10/2001 | Br.ang.nemark | | 433/173 |
| 6,319,000 B1 * | 11/2001 | Br.ang.nemark | | 433/75 |
| 6,439,887 B2 * | 8/2002 | Br.ang.nemark | | 433/173 |
| 6,500,003 B2 * | 12/2002 | Nichinonni | | 433/173 |
| 6,692,254 B1 * | 2/2004 | Kligerman et al. | | 433/173 |
| 6,793,491 B2 * | 9/2004 | Klein et al. | | 433/173 |
| 6,902,401 B2 * | 6/2005 | Jorneus et al. | | 433/173 |
| 6,997,707 B2 * | 2/2006 | Germanier | | 433/75 |
| 7,021,934 B2 * | 4/2006 | Aravena | | 433/173 |
| 7,632,097 B2 * | 12/2009 | De Clerck | | 433/215 |
| 2002/0137003 A1 * | 9/2002 | Knapp | | 433/76 |
| 2002/0160337 A1 * | 10/2002 | Klein et al. | | 433/213 |
| 2002/0177104 A1 * | 11/2002 | Klein et al. | | 433/173 |
| 2002/0192620 A1 * | 12/2002 | Jorneus et al. | | 433/173 |
| 2004/0142300 A1 * | 7/2004 | Aravena | | 433/76 |
| 2005/0019727 A1 * | 1/2005 | McGlumphy et al. | | 433/173 |
| 2005/0170311 A1 * | 8/2005 | Tardieu et al. | | 433/76 |
| 2005/0202370 A1 * | 9/2005 | Brajnovic | | 433/181 |
| 2005/0214717 A1 * | 9/2005 | Freilich et al. | | 433/180 |
| 2006/0093988 A1 * | 5/2006 | Swaelens et al. | | 433/76 |
| 2006/0121410 A1 * | 6/2006 | Aravena | | 433/76 |
| 2006/0223029 A1 * | 10/2006 | Berger | | 433/172 |
| 2007/0160953 A1 * | 7/2007 | Tardieu | | 433/173 |

FOREIGN PATENT DOCUMENTS

| | | | |
|---|---|---|---|
| DE | 375012 | * | 6/1984 |
| DE | 3525298 A1 | * | 1/1987 |
| EP | 0 583 829 A1 | | 2/1994 |
| EP | 583829 A1 | * | 2/1994 |
| EP | 872216 A1 | * | 10/1998 |
| EP | 1 205 159 A1 | | 5/2002 |
| EP | 1 607 063 A1 | | 12/2005 |
| EP | 1607063 A1 | * | 12/2005 |
| FR | 2 623 999 | | 9/1989 |
| JP | 2000-512867 A | | 10/2000 |
| JP | 2004-521671 A | | 7/2004 |
| WO | WO 92/03984 | | 3/1992 |
| WO | 97/49350 | | 12/1997 |
| WO | WO 97/49351 | | 12/1997 |
| WO | WO 9749351 A1 | * | 12/1997 |
| WO | WO 02/062257 A1 | | 8/2002 |
| WO | WO 03/061512 A1 | | 7/2003 |
| WO | WO 2005/053564 A2 | | 6/2005 |
| WO | WO 2005053564 A2 | * | 6/2005 |

* cited by examiner

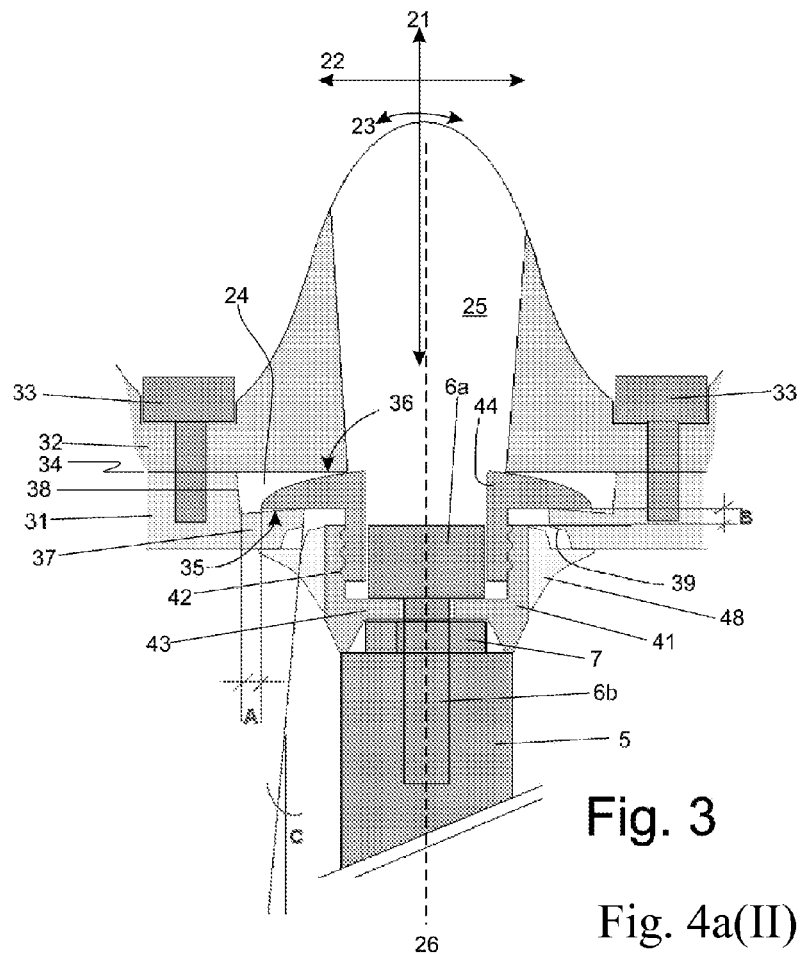
Fig. 3
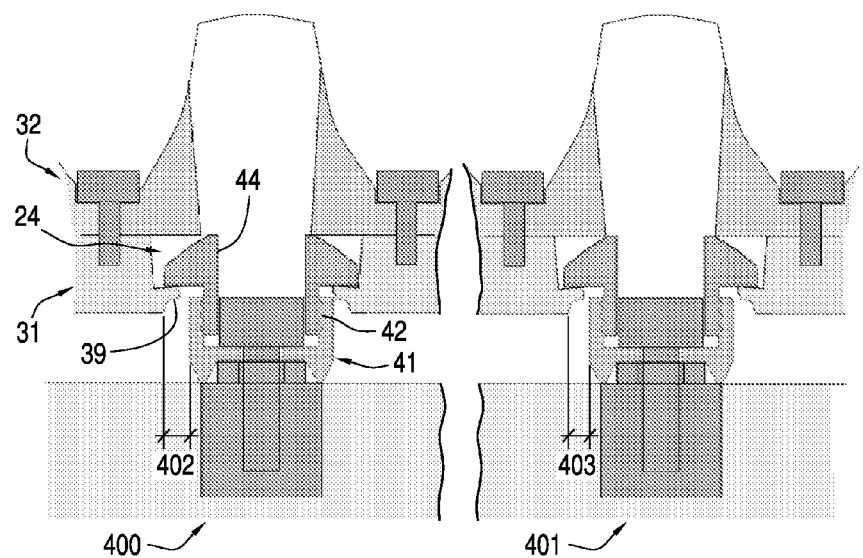
Fig. 4a(I)  Fig. 4a(II)

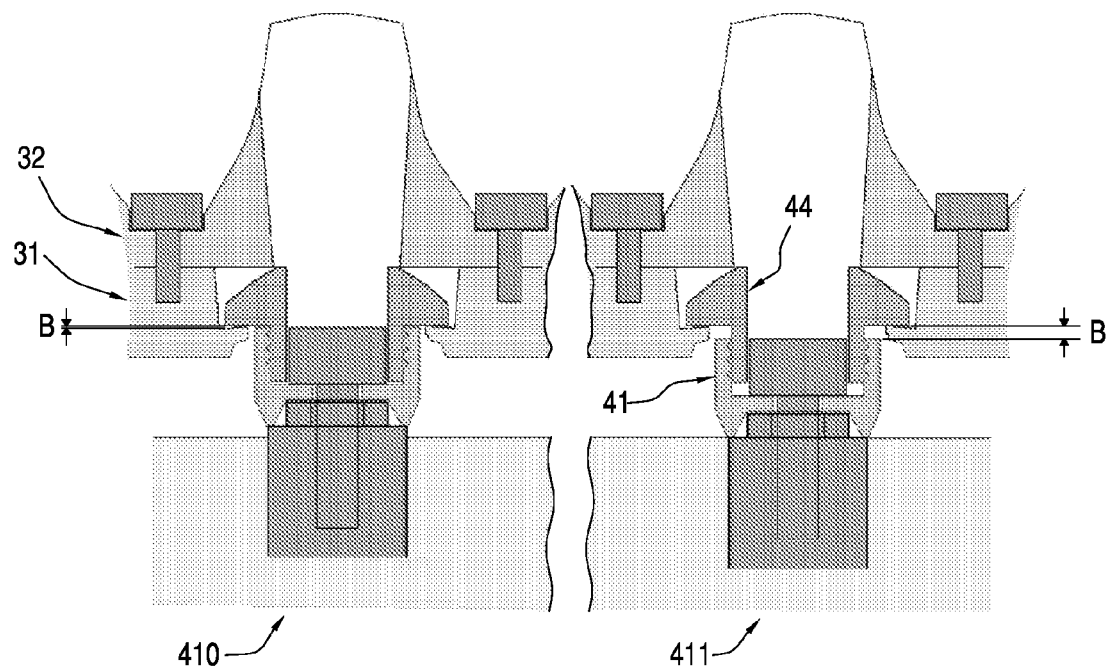
Fig. 4b(I)    Fig. 4b(II)
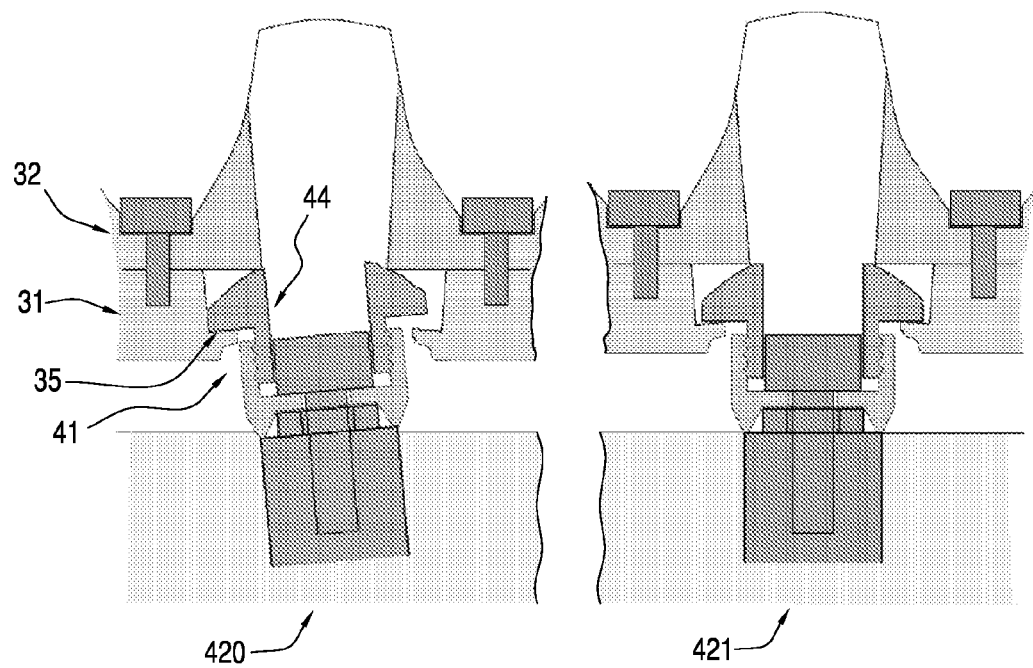
Fig. 4c(I)    Fig. 4c(II)

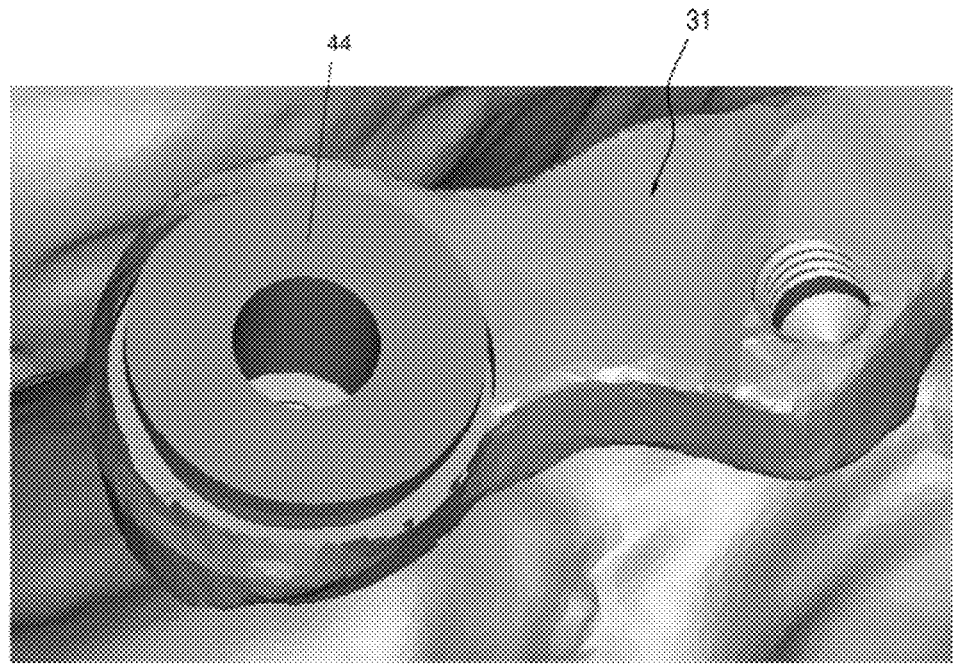
Fig. 12
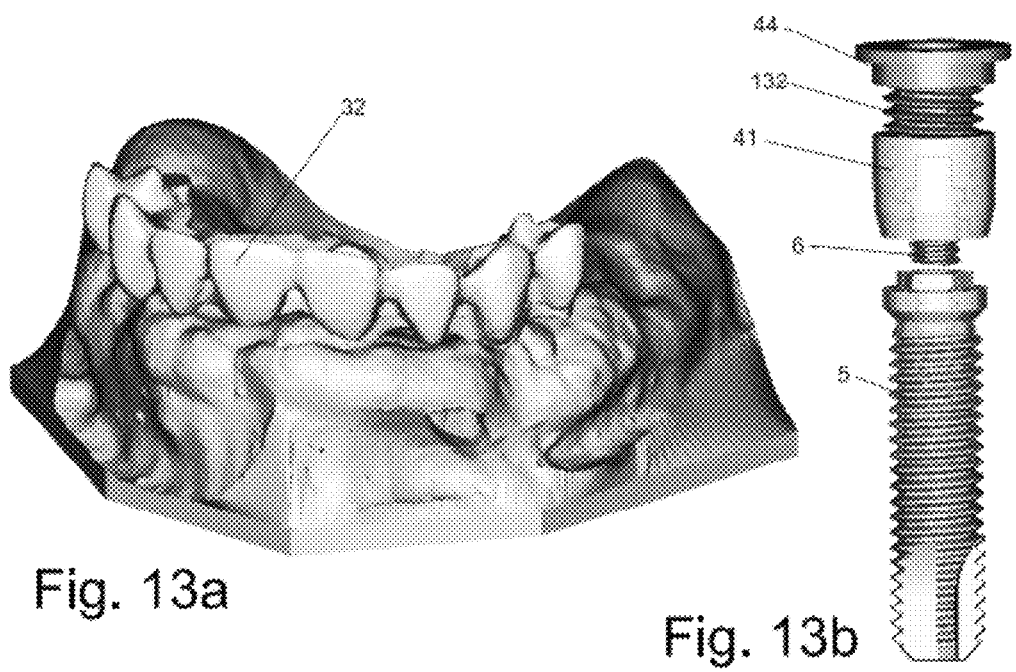
Fig. 13a
Fig. 13b

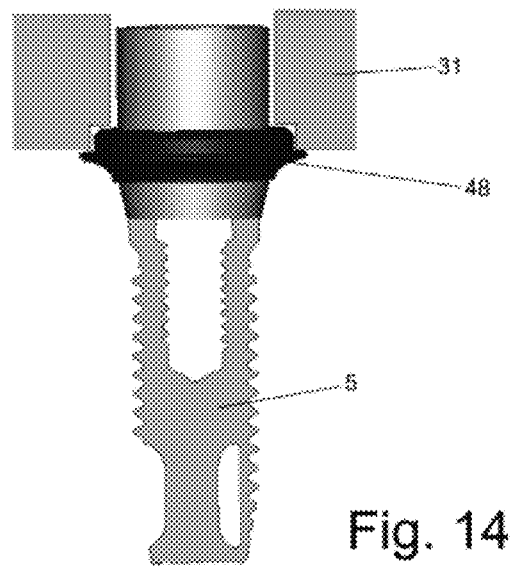
Fig. 14
Fig. 15a 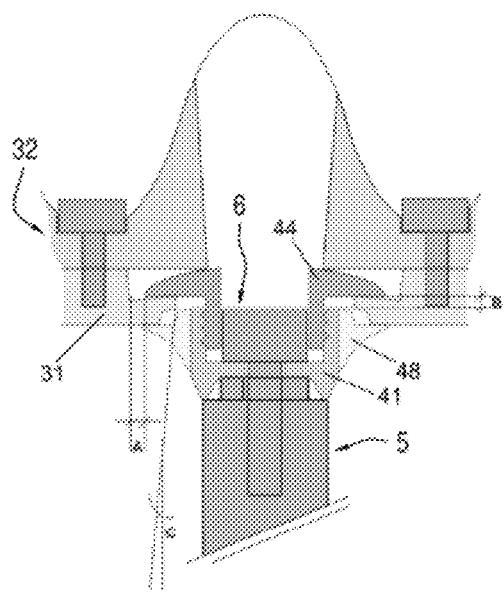 Fig. 15b 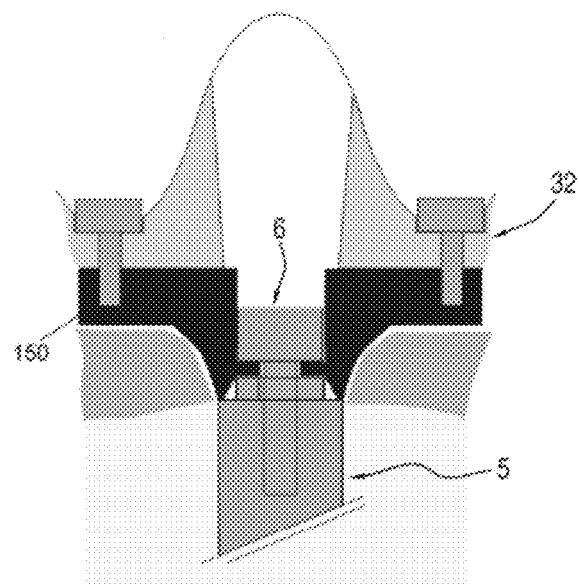

DEVICE FOR SECURING A DENTAL ATTACHMENT TO AN IMPLANT

FIELD OF THE INVENTION

The present invention relates to securing a dental attachment, such as a dental bridge or other dental prosthesis, to a dental implant which has been implanted in a patient's jaw as well as to methods of constructing and using the dental attachment. The invention is particularly relevant when an attachment must be placed on more than one implant simultaneously.

BACKGROUND TO THE INVENTION

It is known to secure a dental attachment, such a dental bridge or other dental prosthesis, to implants which have been implanted into a patient's jaw bone. An attachment can be manufactured after the implant is placed in the jaw bone or before the implant is placed in the jaw bone.

Where the attachment (e.g. bridge) is manufactured after the implants have been installed in the patient, an impression is typically taken of the mouth to determine the locations of the implants relative to the jaw and each other. In such cases, it is possible to plan, with some certainty, the size and shape of the attachment and the attachment is designed to have very limited play with respect to the implants. Some limited adjustment can be provided by recesses in the attachment and the anchorage elements (also known as abutments) on the upper part of the implants. When the attachment is fitted to the implant, cement is applied to the internal surface of the recess of the attachment and the external surface of the abutment to overcome any play between these parts. Cement, or cement-like agents, may pose problems related to hardening. Most cement types harden very rapidly, making it difficult during the hardening process to achieve exact and permanent positions for the bridge. Moreover, cement may be difficult to handle in the mouth of a patient (for example, determining the correct amount of cement to use) and may cause soiling of the restoration site.

Where the attachment is designed and manufactured prior to the installment of the implants—for so-called 'immediate loading'—the amount of play between the attachment and the implant can be considerably larger. The information about the expected implant positions must come from an implant planning system (such as SimPlant™ from Materialise NV, Belgium). The implant planning system allows a clinician to determine the optimal position of the implants in a computer environment showing digital information of the patient (for example CT, images). The implant plan can be used to design and manufacture the attachment and means (e.g. surgical templates such as SurgiGuide™, Materialise NV, Belgium) are used to transfer the planning to the patient. The play between the implants after installation and the attachment depends on the manufacturing tolerances of the bridge and the inaccuracies inherent to the medical imaging for implant planning and the surgical process of transferring the planning to the patient. Typically the play will range from 0 to 0.5 mm in the lateral direction (known as the mesio-distal or bucco-lingual direction), 0 to 0.5 mm in the vertical direction (known as the coronal-apical direction) and 0 to 5° in an angular direction (i.e. rotation about a vertical axis through the implant site). For example, a two-stage procedure can be used. The implants are installed and an impression taken of the post-operative situation several weeks after the surgical intervention. Using impression copings, the exact positions of the implants in the mouth are transferred to a gypsum model. Implant replicas embedded in this model allow a dental technician to manufacture a prostheses that fits exactly on the implants in the jaw of the patient. A disadvantage of this approach is that the prosthesis cannot be produced prior to installment of the implants.

There have been various proposals to provide a degree of adjustment between an implant and an attachment. International Patent Application WO 03/061512 describes a dental attachment with a longitudinally extending recessed wall. An implant has a longitudinally-extending portion which can fit within the recessed wall of the attachment and which can expand to anchor the attachment in a relative longitudinal displacement relative to the portion of the implant. The use of expandable components has the disadvantage that, in the expanded state, recesses are present between the flanges of the expanded component (for instance in the radial direction). These recesses are likely locations for bacteria to settle, possibly causing infections during later stages of treatment. Furthermore, using the expandable abutments, the loads are transferred to the implants by friction. This may cause problems of loosening of the attachment in case of clenching by the patient.

International Patent Application WO 2005/053564 describes a system to overcome lateral misalignments. An anchorage part of an attachment comprises a hole for a retaining screw and the neck of the retaining screw is smaller than the hole in the anchorage part. International Patent Application WO 92/03984 describes a device for anchoring a dental attachment to overcome angular deviations in the play between the bridge and the implants.

Each of the above solutions only permit adjustment of an attachment relative to an implant in a single direction (longitudinal, lateral or angular).

SUMMARY OF THE INVENTION

An object of the present invention is to provide a method of securing a dental attachment, such as a dental bridge or other dental prosthesis and/or to a dental implant which can be, or has been, implanted in a patient's jaw as well as to methods of constructing and using the dental attachment. The present invention seeks to reduce or overcome at least one of the problems of the prior art methods and devices.

A first aspect of the present invention provides a dental attachment assembly for fitting to a dental implant comprising:
  an anchorage unit for fitting to the dental implant; and,
  a dental attachment for mounting to the anchorage unit, the dental attachment comprising a first attachment part and a second attachment part which define an aperture for accommodating a portion of the anchorage unit, with a boundary wall of the aperture on each of the attachment parts serving, in use, as a jaw for clamping against the portion of the anchorage unit.

The invention is particularly relevant when an attachment must be placed on more than one implant simultaneously. Attachment means any structure (with a regular or irregular cross section, regardless of the material used) intended to connect at least two implants and used to transfer loads (for instance as a result of mastication) to these implants. Clamping a dental attachment to an anchorage unit provides a secure connection between these parts and avoids the problems of cement and expandable parts. A further advantage of clamping is that one of the attachment parts can be a functional (i.e. load bearing) part and a second of the attachment parts can be an aesthetic part. If connecting the two parts of the attachment is performed by means other than screws (for example, by the dental equivalent of buttons), a common problem referred to as screw loosening can be avoided. Screw loosening occurs when the small screw used to attach the prosthesis to the implants unscrews and the prosthesis thereby sits less stably on the implants.

An advantage of having the part of the anchorage unit protruding through the attachment is that the size of the attachment can be reduced, which is advantageous in the mouth because of the limitations in space and the functional relation with antagonists.

Preferably, an interface between the first attachment part and the second attachment part is substantially parallel to a longitudinal axis of the attachment (e.g. the attachment is divided into a lower attachment part just above the patient's gums and an upper attachment part.) This considerably eases the fitting of the anchorage units and the attachment parts and allows the interface between the attachment parts to be concealed by overlapping the upper attachment part (which typically carries artificial dentures) over the lower attachment part. For some embodiments it also allows the upper attachment part to be manufactured after the lower attachment part has been successfully fitted to the patient. Thus, if it is found that the lower part does not successfully fit on the set of implants, only the lower attachment part needs to be modified or replaced, without the need to replace an entire attachment. In general a prosthesis for immediate loading will typically not be the final prosthesis. One of the advantages of this embodiment of the present invention is that costs are reduced because only one part of the prosthesis, rather than the entire prosthesis, needs to be re-manufactured. The lower attachment can be accommodated in a recess located on a side of a drilling template facing the treatment site where implants are to be fitted. This allows the implants to be fitted through the lower attachment part, thereby allowing an improved fit.

Preferably, the aperture is of greater size than the portion of the anchorage unit whereby to allow adjustment of the position of the attachment with respect to the anchorage unit. For example, the aperture can have a width which is greater than the portion of the anchorage unit whereby to permit adjustment in at least a lateral direction.

Preferably the anchorage unit comprises first and second anchorage elements which are adapted, in use, to secure at a range of different longitudinal displacements with respect to one another whereby to provide an amount of longitudinal (apico-coronal) adjustment.

Adjustment of the position of the attachment with respect to the anchorage unit in an angular direction can be accommodated by a suitable size of the aperture in the attachment. Alternatively, a rotatable connection can be provided between parts of the anchorage unit.

A second aspect of the present invention provides an anchoring assembly for securing a dental attachment to a dental implant, the assembly comprising:
- a first anchorage element for fitting to a head of the dental implant, and
- a second anchorage element for fitting to the first anchorage element, the first and second anchorage elements together defining a pair of jaws for, in use, receiving and clamping against a portion of the dental attachment.

It will be understood that both aspects of the invention are solutions to the problem of securing an attachment to an implant and share the feature of clamping between an attachment and an anchorage unit.

It is noted that the play between the attachment and the implant may be planned (for example, where a dental attachment is designed prior to implant placement in a patient) or may be unplanned (for example, play which arises from manufacturing tolerances of the attachment). The attachments can be manufactured after the implants are placed in the jaw bone or before the implants are placed in the jaw bone.

An attachment can be located inside a recess of the template. The attachment may be only one piece.

The present invention also provides a method of fitting a dental attachment to at least one dental implant at a treatment site comprising: fitting an anchorage unit to the dental implant; and, clamping a first attachment part and a second attachment part around the anchorage unit, wherein the first and second attachment parts define an aperture for accommodating a portion of the anchorage unit, with a boundary wall of the aperture on each of the attachment parts serving as a jaw for clamping against the portion of the anchorage unit.

The method may include the preliminary steps of: locating the first attachment part inside a recess of a drilling template on a side of the template which will face the treatment site; applying the template to the treatment site; fitting the implant; removing the template and leaving the first attachment part at the treatment site.

The present invention also provides a method of fitting a dental attachment to at least one dental implant at a treatment site comprising: fitting an anchorage unit to the dental implant; clamping a first attachment part and a second attachment part around the anchorage unit to achieve a desired fit, wherein the first and second attachment parts define an aperture for accommodating a portion of the anchorage unit, with a boundary wall of the aperture on each of the attachment parts serving as a jaw for clamping against the portion of the anchorage unit; replacing the first attachment part and anchorage unit with a single part which matches the relative positions of the first attachment part and anchorage unit which achieved the desired fit.

BRIEF DESCRIPTION OF THE DRAWINGS

Embodiments of the invention will be described, by way of example only, with reference to the accompanying drawings in which:

FIG. 3 shows a second embodiment of the invention, in which a two-part attachment clamps around an anchorage unit;

FIG. 4a (I) shows the use of the apparatus of FIG. 3 to adjust in different directions in accordance with a first embodiment;

FIG. 4a (II) shows the use of the apparatus of FIG. 3 to adjust in different directions in accordance with the first embodiment;

FIG. 4b (I) shows the use of the apparatus of FIG. 3 to adjust in different directions in accordance with a second embodiment;

FIG. 4b (II) shows the use of the apparatus of FIG. 3 to adjust in different directions in accordance with the second embodiment;

FIG. 4c (I) shows the use of the apparatus of FIG. 3 to adjust in different directions in accordance with a third embodiment;

FIG. 4c (II) shows the use of the apparatus of FIG. 3 to adjust in different directions in accordance with the third embodiment;

FIG. 12 shows a second part of an anchorage unit fitted to an implant;

FIG. 13a shows an upper attachment part (prosthesis);

FIG. 13b shows the components of the anchorage unit fined to an implant;

FIG. 14 shows sealing between the anchorage unit and attachment;

FIG. 15a shows a comparison of a lower attachment part and anchorage unit used during fitting;

FIG. 15b shows a final lower attachment part resulting from FIG. 15a.

DESCRIPTION OF PREFERRED EMBODIMENTS

Figure 1:
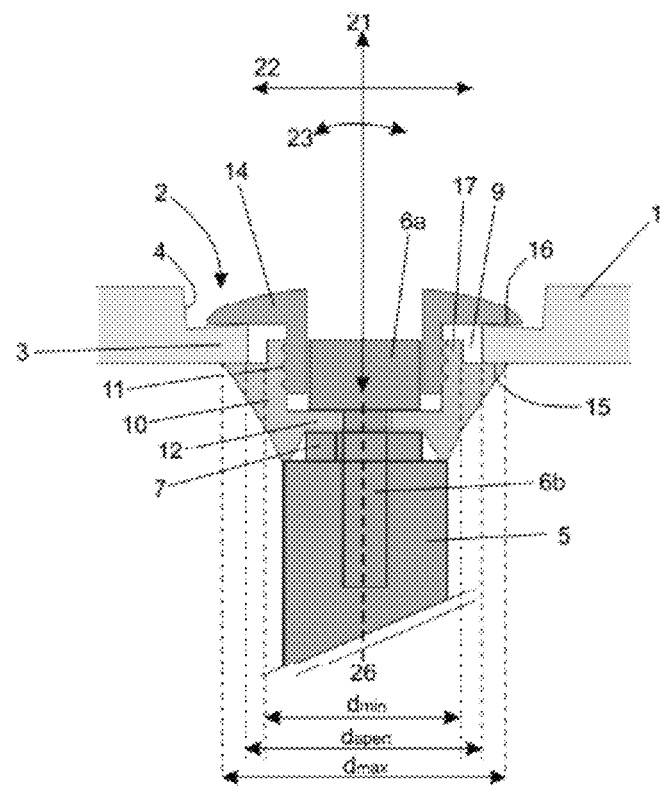
FIG. 1 shows a first embodiment of the invention, in which a two-part anchorage unit clamps around an attachment.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. FIG. 1 shows a first embodiment of the invention. A dental implant 5 is embedded with the jawbone of a patient. An attachment (e.g. dental bridge) 1 comprises an aperture 2 in the region where the attachment 1 is required to be fitted to the dental implant 5. The term attachment means any structure (with a regular or irregular cross section, regardless of the material used) intended to connect at least two implants and used to transfer loads (for instance as a result of mastication) to these implants.

The attachment 1 has a flange 3 which projects partially across the aperture 2 to form a stepped edge region. A two-part anchorage unit 10, 14 secures the attachment 1 to the implant 5. The anchorage unit comprises a first, lower, part 10 and a second, upper, part 14. The lower part 10 has a collar 12 with a central aperture to accommodate the shaft 6b of a fixing screw. In use, collar 12 of part 10 firmly engages with the connective part of implant 5 by screw head 6a. FIG. 1 shows part 10 also sitting on top of implant 5 in addition to being held against abutment 7. It is desirable that part 10 should have a good fit to the implant to minimise the possibility of bacteria settling in the interface. In this example part 7 is an integral part of the implant 5. However, many types of implant designs may be used with the present invention. Part 7 can be an external hexagonal connection) for example. In other implant designs the connection will be internal.

Part 10 has a collar with a radially extending surface 15. Surface 15 serves, in use, as a jaw to connect to flange 3 of the attachment 1. Upper part 14 of the anchorage unit fits within part 10 and an interface 11 allows parts 10 and 14 to be secured in a desired position with respect to one another (in direction 21). Interface 11 can comprise a screw thread, a clip, or another interlock which allows the parts 10, 14 to be held tightly in a desired position. The inner diameter of part 14 is larger than the outer diameter of screw head 6a to allow head 6a to pass within. Part 14 has a jaw 16 in the form of a radially extending surface. In use, jaws 15, 16 act as a clamp to grasp flange 3 of the attachment 1 to tightly secure the attachment 1 to implant 5.

If required, silicon O-rings or the like (not shown) may be positioned between the parts 10, 14 of the anchorage unit and the attachment 1 to ensure proper sealing of the aperture 2. The attachment 1 can be manufactured from any material suitable for dental prosthetics such as metal, carbon-fibre reinforced plastic, ceramics, etc. It can be either a final or a temporary dental reconstruction and may (for example, in the case of a metal attachment with porcelain) or may not (for example in the case of a metal bar for an overdenture) have a prosthetic finish.

The apparatus shown in FIG. 1 permits adjustment in several different directions. Three directions 21, 22, 23 are shown. Direction 21 will be called the axial or longitudinal direction as it is parallel to the longitudinal axis 26 of an implant. This is also known as apico-coronal direction. Direction 22 will be called the lateral or radial direction as it is a shift which is in the radial direction of an implant, and laterally across the surface of the patient's gums. This direction is also known as mesio-distal (side-to-side across the mouth) or bucco-lingual (forwards-to-backwards). Direction 23 will be called the angular direction as it represents an angular rotation with respect to the longitudinal axis 26 of the implant. The terms bucco-lingual, mesiodistal, apico-coronal are well known in the field.

Part 10 of the anchorage unit has a cylindrical shaft 17 which supports, on an inner surface, an interface 11. The outer diameter of the shaft 17 ($d_{min}$) is smaller than the diameter of aperture 2 ($d_{apert}$) in the attachment 1. The outer diameter ($d_{max}$) of the jaw 15 is larger than the diameter ($d_{apert}$) of the aperture 2. This provides an amount of clearance 9 between the shaft 17 and attachment 1 while ensuring that the attachment can still be clamped by surface 15. Similarly, the outer diameter of upper part 14 of the anchorage unit is smaller than the diameter of the aperture 2 in attachment 1 (the diameter being defined by a wall 4) to provide an amount of clearance. The clearance described above permits an amount of adjustment, in a lateral direction 22, when positioning the attachment 1 with respect to the implant 5. The clearances described above also permit the attachment 1 to be secured to an implant 5 which has been fitted at an angle which is inclined with respect to vertical. The upper face of flange 3 is inclined. This allows part 14 to be inclined without drastically increasing the length of shaft 17, which supports the interface 11.

Figure 2:
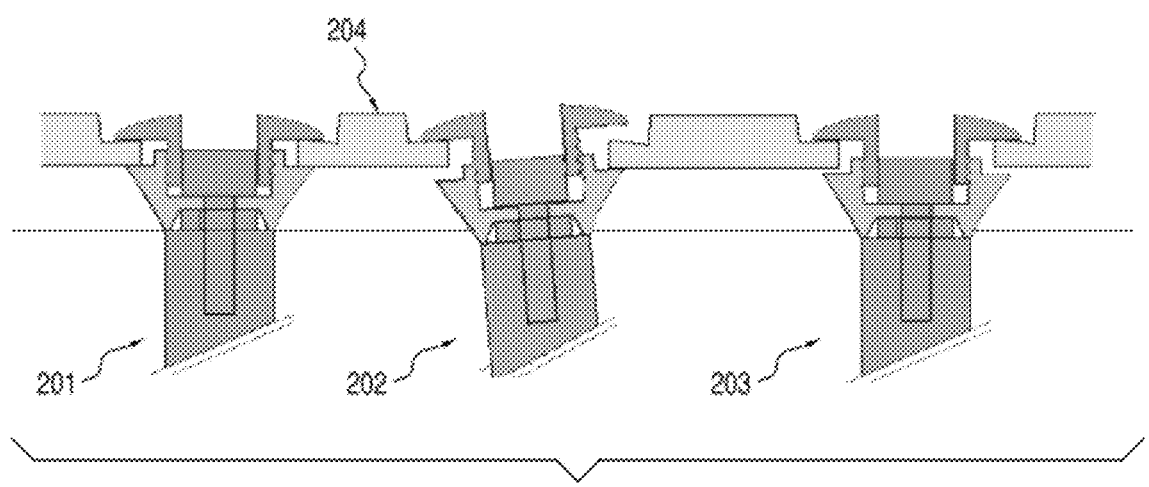
FIG. 2 shows the use of the apparatus of FIG. 1 at different implant sites adjusted in different directions to different implants having different orientations.

FIG. 2 shows an example of an attachment 204 which fits to a set of three implants fitted in different positions at implant sites 201, 202, 203. At each of the implant sites, a two-part anchorage unit connects to the attachment. For the purpose of illustrating the invention, each of the three anchorage units are shown providing adjustment in a different one of the three possible adjustment directions described above. The attachment 204 is secured to the dental implants by using different clamping actions based on the position of the dental implants provided at the three implant sites 201, 202, 203. As seen in FIG. 2, the dental implant at implant site 203 is set below a horizontal plane. An anchorage unit can then be adjusted in a vertical direction to prevent the attachment 204 from moving in an upward direction. As seen in FIG. 2, the dental implant at implant site 203 is set at an angle. In order to properly secure the attachment 204 at this site, while still providing proper fitting at implant sites 201 and 203, an anchorage unit can be adjusted to clamp the attachment 204. Movement of the attachment in the downward direction is then limited by the anchorage units at sites 201, 202.

In FIG. 1 the attachment 1 has a stepped cross-section in the region of the aperture 2 to provide a flange 3 having a reduced depth (in direction 21) compared to the normal depth of attachment 1. It is not essential to provide this stepped cross-section, and parts 10, 14 of the anchorage unit can clamp against the upper and lower surfaces of the attachment.

FIG. 3 shows a second embodiment of the invention. This embodiment uses the same principle of securing an attachment to an implant by clamping as FIG. 1. However, in FIG. 3 a two-part attachment 31, 32 clamps against an upper anchorage unit 44 of an anchorage unit 41, 44 fitted to the implant 5. As before, a dental implant 5 is embedded with the jawbone of a patient. An attachment (e.g. dental bridge) is formed in two parts: a lower attachment part 31 and an upper attachment part 32. The two attachment parts 31, 32 join along an interface 34 which is substantially parallel to the upper surface of patient's jaw and substantially perpendicular to the longitudinal axis 26 of an implant. The two attachment parts 31, 32 are held together by fixing screws 33 or the like (clips for example). The attachment parts define an aperture having a chamber 24 and central shaft 25 in the region where the attachment is required to be fitted to the dental implant 5. The aperture having central shaft 25 connects an upper face of attachment part 32 with a lower face of attachment part 31. The central shaft 25 is at least as wide as the head 6a of the fixing screw 6 and serves to allow access to the implant. The chamber 24 of the aperture, in the region of interface 34, has a greater width to define a chamber for receiving a portion of the anchorage unit. In this embodiment chamber 24 is located within the lower attachment part 31. Chamber 24 accommodates a flanged head of upper anchorage unit 44. The lower attachment part 31 has a flanged portion 37 which projects partially across the chamber 24 to form a stepped edge region. Flanged portion 37 has an upper surface 35 which serves as a first jaw. Upper part 32 has a lower surface 36 which serves as a second jaw. In use, attachment parts 31, 32 clamp tightly against the head of part 44 of the anchorage unit. Chamber 24 is designed so that attachment parts 31, 32 will always seal tightly against one another and clamp against the head of upper anchorage unit 44. The shape of chamber 24 and the head of part 44 is designed to facilitate this. Flange 35 is inclined to allow rotation of upper anchorage unit 44. The head part of upper anchorage unit 44 is curved such that when upper anchorage unit 44 is inclined the head can move freely within the aperture while maintaining circular line contact with the upper part 32 of the attachment.

Anchorage unit 41, 44 is broadly the same as previously described with relation to FIG. 1. As previously described, the two-part anchorage unit 41, 44 engages with the connection part 7 of the implant 5. The anchorage unit comprises a first, lower, part 41 and a second, upper, part 44. The lower part 41 has a collar 43 with a central aperture to accommodate the shaft 6b of a fixing screw. In use, collar 43 of part 41 is firmly engages with the connection part 7 of implant 5 by screw head 6a. Upper part 44 of the anchorage unit fits within part 41 and an interface 42 secures parts 41 and 44 in a desired position with respect to one another in direction 21.

An O-ring (e.g. silicon) or other sealing element 48 fits around part 41 of the anchorage unit and provides a seal between part 41 of the anchorage unit 41 and the lower attachment part 31.

The apparatus shown in FIG. 3 permits adjustment in several different directions. Firstly, adjustment in the lateral direction 22 will be considered. FIG. 3 illustrates a clearance (A) between the outer circumference of part 44 and wall 38 of lower attachment part 31. Similarly, as seen in FIG. 4a (I) at implant site 400, there is clearance 402 between the outer diameter of lower anchorage unit 41 of the anchorage unit and surface 39 of the lower attachment part 31 (seal 48 is flexible). As seen in FIG. 4a (II) at implant site 401, the lower attachment part 31 and anchorage unit are configured to allow the adjustment of the anchorage unit by shifting attachment part 31 to have a smaller clearance 403 in a lateral direction 22. The maximum extent of lateral adjustment is reached when the head of upper anchorage unit 44 rests against wall 38. FIGS. 4a (I) and (II) show how the apparatus of FIG. 3 can be used to provide adjustment in the lateral direction as indicated by the difference in clearance distances with respect to clearances 402 and 403 between the surface 39 of lower attachment part 31 and the lower anchorage unit 41. The configurability of the anchorage units 41, 44 allow the adjustment and fixing of the attachment parts at different implant sites 400 and 401 having different orientations. In other words, at implant site 400, one end of the head of upper anchorage unit 44 abuts the wall, while the other end forms a clearance 402. On the other hand, by having the chamber 24 of the aperture larger than the head part 44, the attachment can be fit at a different implant site by lateral adjustment to have a smaller clearance 403.

Secondly, as seen in FIGS. 4b (I) and (II), adjustment in the longitudinal direction 21 will be considered when the attachment is attached to dental implants having different horizontal orientations. FIG. 3 shows that anchorage units 41 and 44 can be secured at a desired position along the longitudinal axis 26 via interface 42. FIGS. 4b (I) and (II) show that the apparatus of FIG. 3 facilitates an adjustment B in the longitudinal direction by showing that the value of B can either be reduced until the head of part 44 rests on part 41 as seen at implant site 410 (FIG. 4b (I)), or increased until some minimum overlap of the respective collars of anchorage units 41, 44 is reached as seen at implant site 411 (FIG. 4b (II)). As attachment 31, 32 is directly secured to upper anchorage unit 44, this causes the attachment to be positioned at a desired position (in direction 21) above implant 5. The lateral adjustability of the anchorage unit allows the attachment to be attached securely to the dental implants at the implant sites.

Thirdly, adjustment in the angular direction 23 will be considered. Parts 31, 41 and 44 are shaped to permit some adjustment in this direction. Surface 39 of the lower attachment part 31 has a stepped profile to accommodate movement of lower anchorage unit 41. The inclined upper face of jaw 35 allows the head of upper anchorage unit 44 to slide along the jaw, during a fitting operation, to a desired fixing position. The chamber 24 formed by the aperture in lower attachment part 31 and the upper attachment part 32 has a depth which is sufficient to accommodate the head of upper anchorage unit 44 at different angular positions C, while still being able to clamp against the head of upper anchorage unit 44. The depth of chamber 24 of the aperture, and the convex shape of the head of upper anchorage unit 44 allows upper anchorage unit 44 to be maneuvered in the angular direction 23. FIGS. 4c (I) and (II) show how the apparatus of FIG. 3 can be used to provide adjustment at different implant sites 420, 421 having implants with different angular directions to securely clamp a lower attachment 31. For example, as seen in implant site 421 (FIG. 4c (II)), no angular adjustment by the anchorage units is needed for securing the lower attachment 31. However, at implant site 420 (FIG. 4c (I)), the dental implant has an angular orientation. Although the attachment parts 31, 32 are firmly pressed together, jaw 35 of the lower anchorage unit 31 has an inclined surface to accommodate the head of upper anchorage unit 44 to allow the adjustment of the anchorage units 41, 44. This configuration allows the secure clamping of the lower attachment part 31 at both implant sites 420 and 421, while avoiding the problems of cement and expandable parts.

Part 41 of the anchorage unit 41 can be fitted to the head of implant 5 (e.g. as part of a fixture mount) before the implant is installed in the patient.

Figure 5:
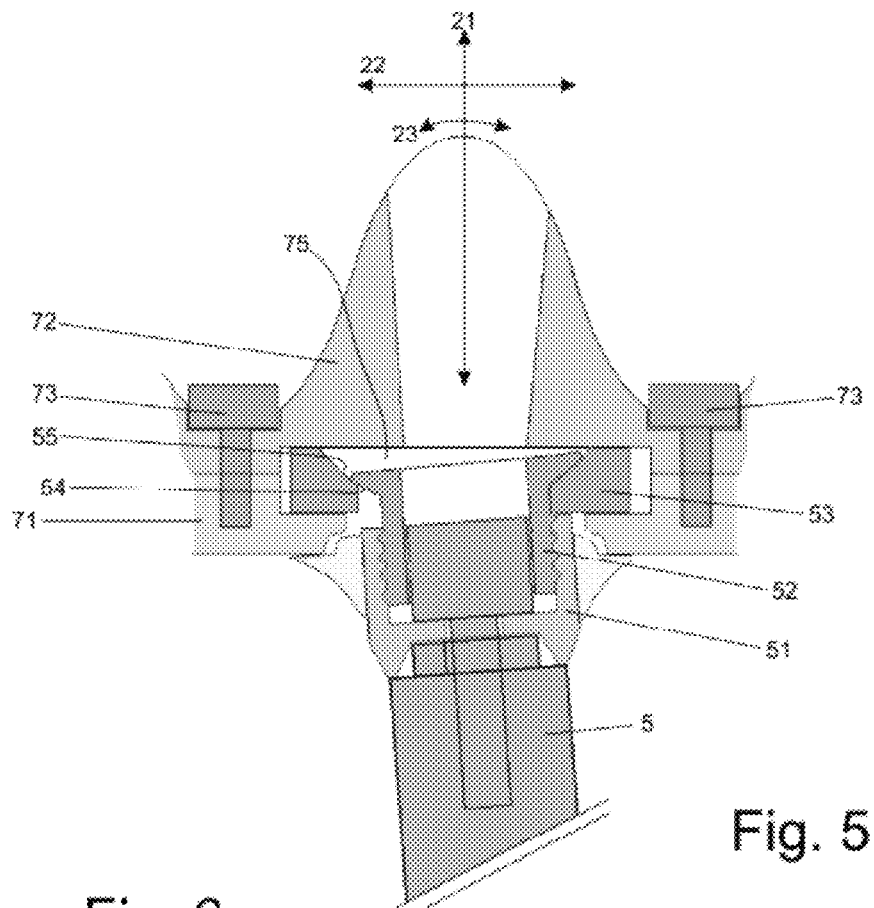
FIG. 5 shows a third embodiment of the invention, in which the anchorage unit comprises three parts.

FIG. 5 shows a modification to the embodiment shown in FIG. 3. In this embodiment the anchorage unit, which connects the implant 5 to the attachment 31, 32, comprises three parts 51, 52, 53. As before, anchorage unit comprises a first part 51 which is mountable to implant 5 and a second part 52 which fits within the first part 51 at a selected offset in the longitudinal direction. An annular head of part 52 has a convex lower surface 54. A third part 53 of the anchorage unit has an annular shape and has a concave upper surface 55. Surface 54 of part 52 and surface 55 of part 53 have complementary sizes and shapes to allow the respective parts 52, 53 to slide across one another to a required angular position. The interior diameter of part 53 is wider than the outside diameter of the cylindrical body of part 52 to permit an amount of angular movement (FIG. 5 shows the apparatus turned fully anticlockwise so that the cylindrical body of part 52 abuts part 53). A two-part attachment 71, 72 clamps around part 53 of the anchorage unit using fixing screws 73 or the like. FIG. 5 shows parts 71 and 72 each having an aperture to provide a cavity 75 to accommodate annular part 53. Alternatively, the aperture can exist in just the lower attachment part 71. Chamber 75 is wider than the outer diameter of annular part 53 to permit adjustment in the lateral direction 22. The apparatus shown in FIG. 5 has an advantage of more securely supporting the attachment 71, 72 to the implant 5 in angular orientations. Chamber 75 is the same height as annular part 53 as there is no need for the chamber 75 to accommodate angular movement of part 53, this instead being achieved through the rotatable connection between parts 52, 53 of the anchorage unit. There is no need to fix parts 52 and 53 together. As soon as an attachment is placed on more than one implant simultaneously, parts 52 and 53 cannot move because this would require an angular movement of the attachment, which will be blocked by the anchorage unit(s) on the other implant(s).

Another way to achieve movement in the lateral direction is to modify part 51 to the way shown in WO2005/053564. In this case, aperture 75 can be exactly the same size as part 53.

Figure 6:
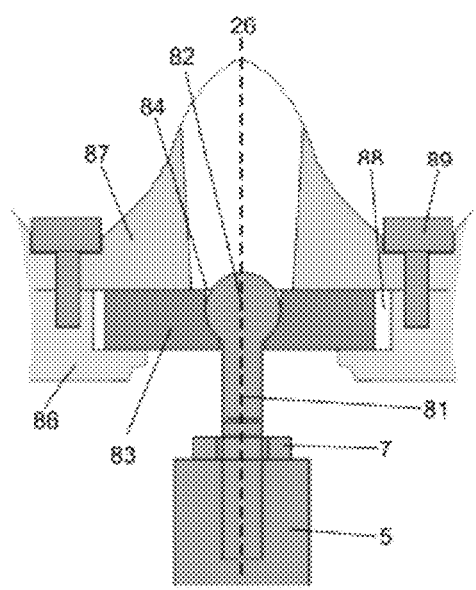
FIG. 6 shows a fourth embodiment of the invention.
Figure 7:
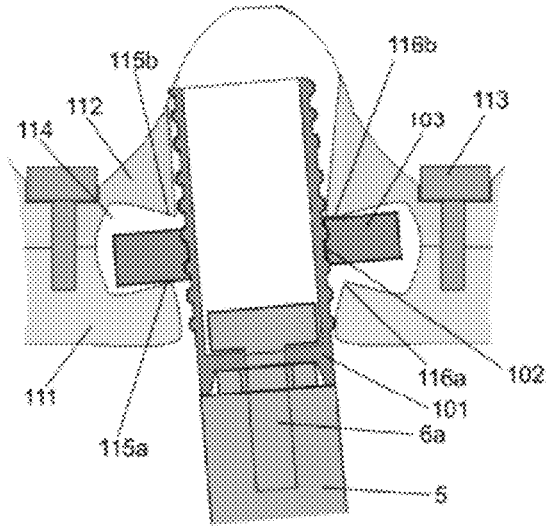
FIG. 7 shows a fifth embodiment of the invention.

FIGS. 6 and 7 show two further embodiments which are particularly effective at securing an attachment to an implant at various angular orientations. In FIG. 6, a shaft 81 is mounted to implant 5. The shaft 81 has a ball-shaped head 82. A disc-shaped part 83 has a central hole 84 which serves as a socket. The hole 84 is sized to accommodate head 82 and to permit a range of angular movement between disc 83 and head 82.

A two-part attachment 86, 87 clamps around disc 83 using fixing screws 89. A cavity 88 to retain part 83 is provided by apertures in one, or both, of attachment parts 86, 87. This cavity preferably is wider than disc 83 to permit an amount of lateral adjustment. Shaft 81 can be fixed in implant in a single mounting position but preferably shaft 81 may be positioned at a selected depth within implant 5 by screw fitting or other suitable fixing which permits a range of fixing depths in direction 21.

In FIG. 7, a cylindrical part 101 is mounted to the head of implant 5 and secured to the implant by a fixing screw 6a. A disc-shaped part 103 can be fixed at a desired position along part 101 by a screw thread or other suitable fixing on the interface 102 between parts 101, 103. Part 103 has an internal diameter which is just larger than the outer diameter of part 101. Attachment parts 111, 112 are held together by fixing screws 113 to define a generally crucifix-shaped internal cavity having a central shaft and left and right-hand chambers 114. Each of the left and right-hand chambers 114 narrow in the region where they join the central shaft. These narrower regions define jaws 115a, 115b, 116a, 116b. In the orientation shown in FIG. 7 jaw 115a presses against a lower side of part 103 and jaw 116b presses against the upper side of part 103 whereby to clamp the part 103. The cavity within attachment parts 111, 112 is wider than parts 101, 103 to permit adjustment in the lateral and angular directions.

In each of the embodiments described above the clamping surfaces of the anchorage unit and/or the attachment can be provided with means to increase the friction between the anchorage unit and the attachment. Such means could, for example, comprise small teeth that bear down on to the clamped part, granules (grains) interlocking into one another respectively on the clamping and the clamped parts or a material with high coefficient of friction (e.g. rubber) applied to the respective surfaces.

In each of the embodiments shown in FIGS. 3-7 the upper attachment part 32 can be part of the final reconstruction while the lower attachment part can be a temporary construction.

Figure 8:
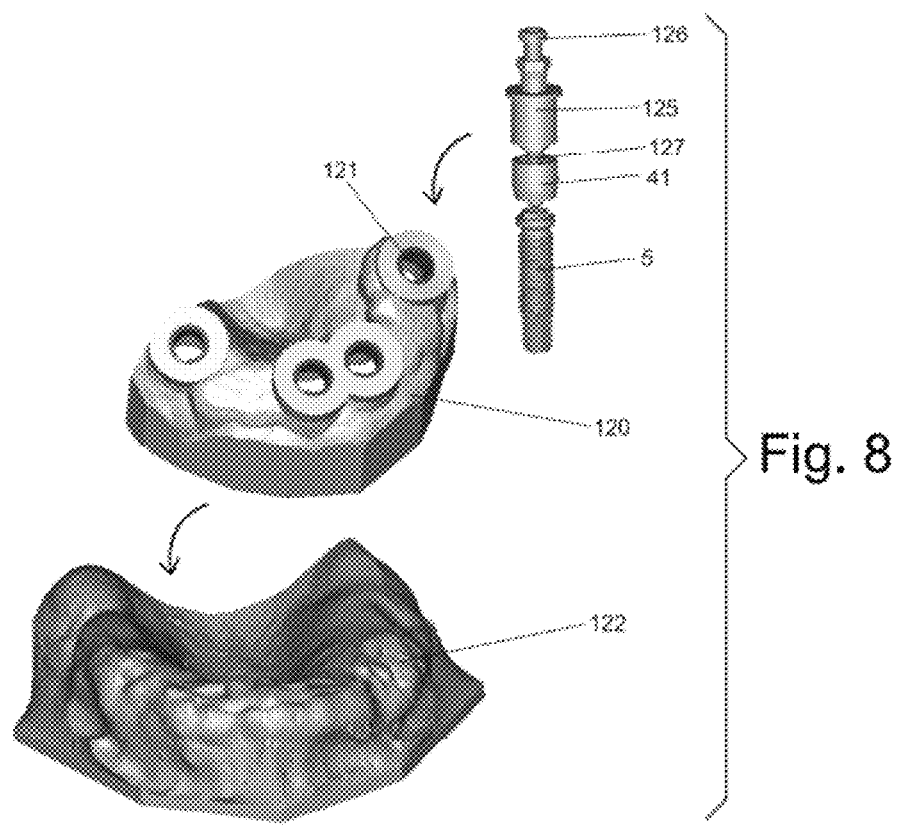
FIG. 8 shows a surgical template and an implant assembly for fitting to a patient.

FIGS. 8-14 show a sequence of steps of a process for installing implants in the mouth of a patient and for fitting an attachment to the implants. The apparatus of FIG. 3 is used as an example, although any of the apparatus of the present invention could be used in this method. Prior to the step shown in FIG. 8, a treatment planning process plans the position of implants in a patient's mouth. This typically involves mapping the patient's mouth by use of a mould or a computerised scanning process. Part of this planning process includes choosing sites to install implants. A surgical template 120 is created to help in accurately transferring the treatment planning to the patient's mouth. The template 120 is shown in more detail in FIGS. 8 and 9a, 9b. FIG. 8 shows that the surgical template 120 exactly fits onto the gums 122 of the patient. The template 120 has a set of holes 121 which match the positions where implants are required to be fitted. Template 120 also holds the lower part 31 of a two-piece attachment as shown in FIG. 3. As seen in FIG. 9a, template 120 is designed to hold the lower attachment part 31 in a cavity 124 on the bottom side (i.e. the side that engages with the patient) which has exactly the shape as the lower attachment part 31, with no undercuts so the attachment part can still be removed. After production of the template 120 the attachment part can simply be mounted into position by inserting it in the cavity 124. As soon as the template 120 is positioned on the patient the attachment part 31 can no longer move. Because the implants 5 are now fitted to the patient by passing them through the lower attachment part 31, there is an increased likelihood that the implants 5 will be correctly placed in positions which allow immediate attachment.

Figure 9A:
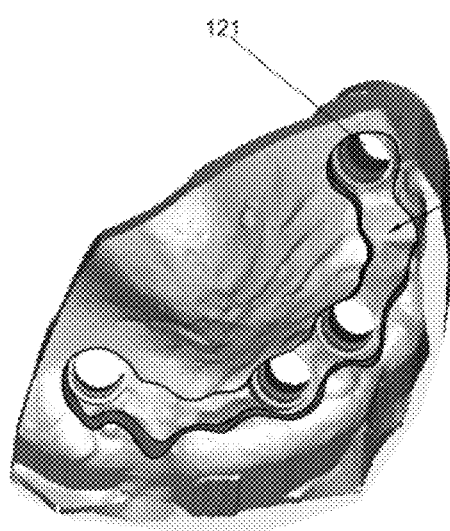
FIG. 9a shows the surgical template of FIG. 8 in more detail.
Figure 9B:
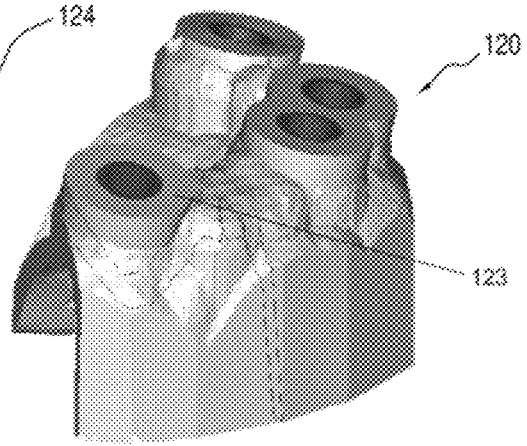
FIG. 9b shows the surgical template of FIG. 8 in still more detail.
Figure 10:
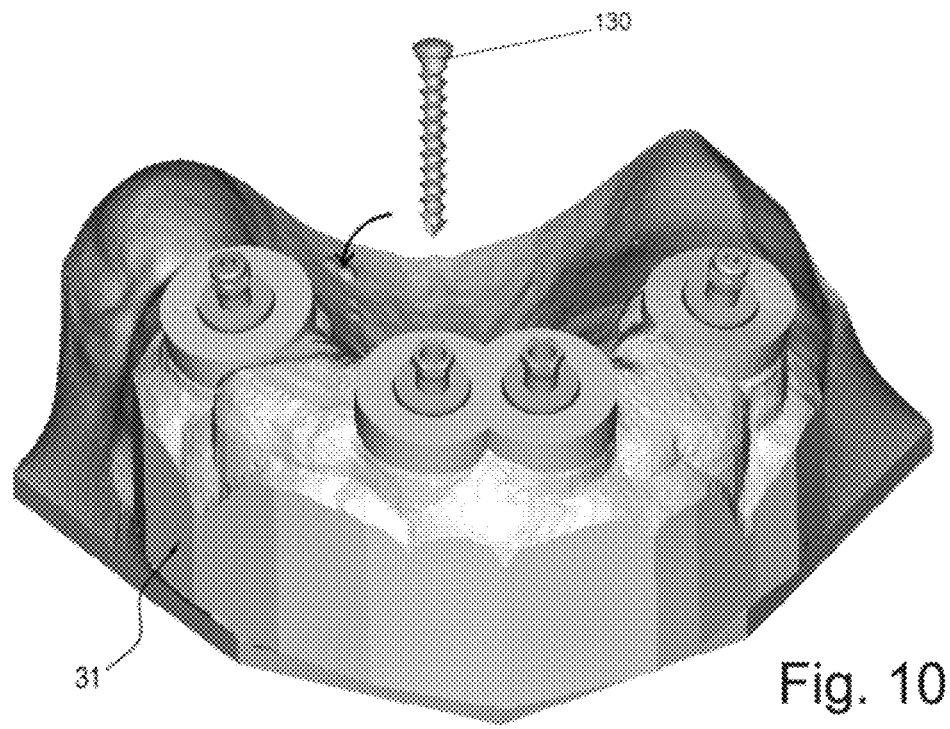
FIG. 10 shows the template after implants have been installed.

Prior to placing the surgical template 120 on the patient, a thin layer of an inert filler such as silicon is applied onto the down-facing (i.e. gingival) side of the lower attachment part 31. This silicon layer fills any gaps between the soft tissue and the template 120 when positioning the latter on the patient and acts as a spacer between the lower attachment part 31 and the soft tissue of the patient. As seen in FIG. 9b, each hole of the template is defined by a guide tube 123 which indicates the correct position and inclination of the implant. An implant 5 is installed through one of the holes 121. Attached to the head of an implant 5 is the first, lower, part 41 of the anchorage unit. Together, the implant and part 41 are mounted on an implant holder 125, with implant holder screws 126 keeping the assembly together. The implant holder 125 engages with part 41 via a tooth-and-groove connection 127 to transfer the torque applied to the holder 125 to part 41 and implant 5 during implant installation. Referring to FIG. 10, the lower attachment part 31 can be secured by screws 130 which are fixed into the bone of the patient, engaging with holes in the lower attachment part 31 which are provided in advance for this purpose. Screws 130 are separate fixings from the implants. Typically osseosynthesis screws are used which do not present any added risk of infection.

By fixing the lower attachment part 31, the surgical template 120 is also fixed. Small shifts of the template 120 during surgery due to handling of the template inside the mouth can no longer occur. As the surgical template 120 holds the lower attachment part 31, fixing the lower attachment part 31 also serves to stabilise the template 120 on the gums 122. Also, fixing the lower attachment part 31 to the bone allows the template 120 to be subsequently removed easily without removing the attachment part 31 itself.

Figure 16:
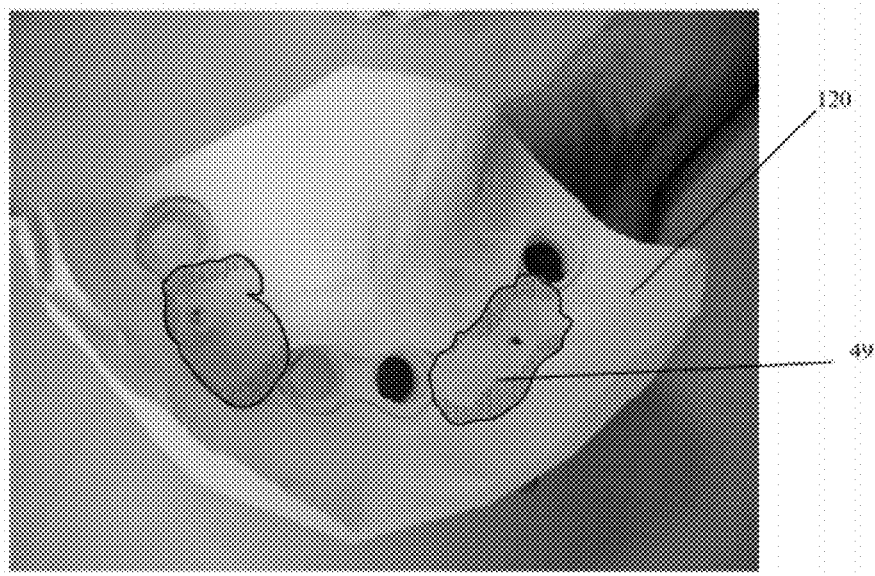
FIG. 16 shows a view of a template according to embodiments of the present invention from the gingival side.
Figure 17:
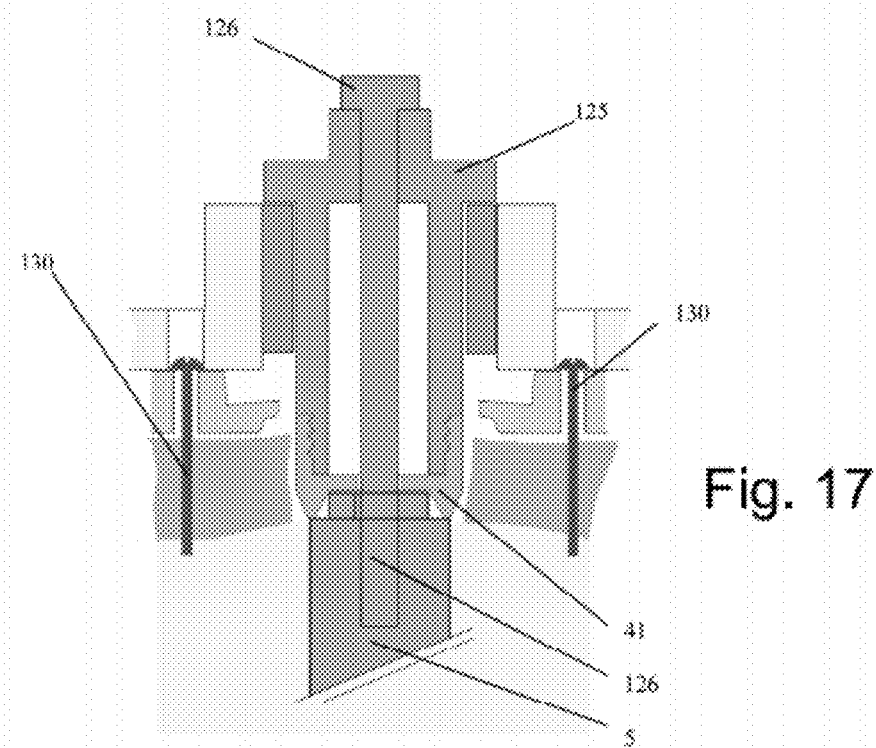
FIG. 17 shows temporary fixation of the lower attachment using osseosynthesis screws according to an embodiment of the present invention.

As further explanation, the lower attachment 31 can be placed inside the recess 124 of the template 120 as shown in FIG. 16. To make sure it does not fall out during the manipulation of the template before it is seated on the recipient site in the mouth of the patient, some suitable holding of filling material 49 may be applied, e.g. silicon. Once the template 120, with the attachment 31 slotted into it has been correctly positioned on the patient some osseosynthesis screws 130 may be applied through the holes in the template 120 that firmly lock the lower attachment 31 onto the recipient site—see FIG. 17. In this manner not only the attachment but also the guide are stable. The guide is in fact stabilized further because of the interaction with the lower attachment. However because the osseosynthesis screws 130 work directly on the attachment, the template itself is not "screwed down". Once the implants have been installed and the implant holders have been removed, the guide can be removed. The lower attachment 31 however is kept in position thanks to the screws 130. Further along the intervention, the lower attachment 31 is anchored by means of the anchorage parts. At that point the ossesynthesis screws 130 are removed. The apertures in the lower attachment 31 through which the ossesynthesis screws 130 were placed then function as recipient sites for small screws 33 that allow upper and lower attachments to be connected as shown in FIG. 3, for example, although any of the apparatus of the present invention could be used in this method.

Figure 11:
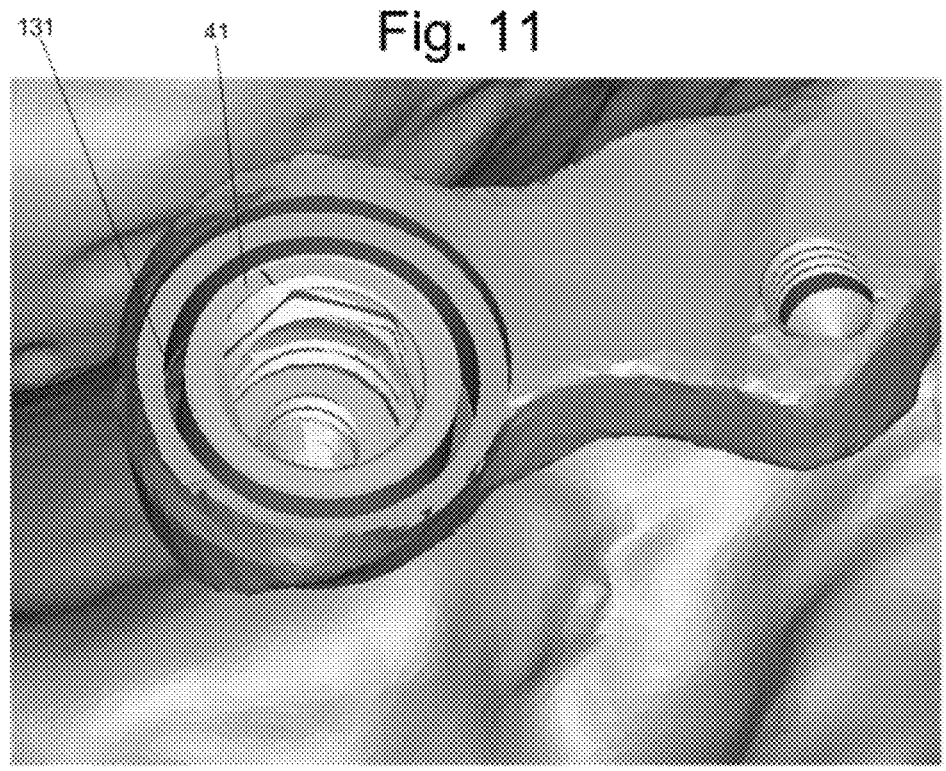
FIG. 11 shows one part of an anchorage unit fitted to an implant.

FIG. 11 shows one implant installed in the jaw. The implant holder 125 and the template 120 are removed after installation, leaving in place the lower attachment part 31. The implant holders 125 are removed one at a time, replacing the implant holder screws 126 with fixture screws 6, firmly locking the abutting pieces 41 into position on the implants 5. As can be seen in FIG. 11, there is clearance 131 between the apertures in the lower attachment part 31 and abutting piece 41. The other screw hole shown in FIGS. 11 and 12 is for receiving a screw (33, FIG. 3) which will keep the upper and lower attachment parts together.

The second, upper, part of each of the anchorage units are fixed onto the abutting pieces 41. As shown in FIGS. 12 and 13b, the second part 44 engages in the abutting piece 41 via a screw thread 132 provide on its outer surface (interface 42, FIG. 3). The second piece 44 is screwed down until its head contacts with the lower attachment part 31, as can be seen in FIG. 12. Any play between the lower attachment part 31 along the axes of the implants relative to what was intended is compensated by screwing the two pieces 41, 44 of the anchorage units together to a greater or lesser degree. The screws 130 fixing the lower attachment part 31 to the jaw bone are then removed. As seen in FIG. 13a, the upper attachment part 32 is then placed onto the lower attachment part 31 and fixing screws 33 are fitted and tightened to rigidly clamp the attachments parts 31, 32 to the anchorage unit. By removing the screws 130 at this stage, change in the position of the lower attachment part is prevented. Deviations from the desired positions are generally small enough not to have the requirement of removing the screw 130 earlier. Optionally, the screw can be removed earlier (e.g. directly after fitting the first part 41 of the anchorage unit) so that the attachment part 31 can be moved into position with respect to the set of implants.

FIGS. 15a and 15b show an alternative final stage. The attachment parts 31, 32 and anchoring unit 41, 44, as seen in FIG. 15a, are removed from the set of implants by unscrewing fixture screws 6. FIG. 15b illustrates when the upper attachment part 32 is removed from the remainder of the assembly and a final part 150 FIG. 15 is formed which has the shape of the set of parts 31, 41, 44, 48. This new, final, part 150 is secured to upper attachment part 32 and then placed upon the set of implants 5 and secured to the implants 5 by reaffixing screws 6. This alternative scheme has an advantage of creating a final part 150 which lacks any gaps between parts. This can provide a much better sealing against the gum. The shape of the final part 150 is determined by transferring the final implant positions after healing to the design environment, e.g. either directly via scanning or indirectly by first transferring them to a working model e.g. a gypsum cast, which is scanned afterwards. Given the known position of the implants and the known dimensions of the upper part of the attachment the design can be performed accurately.

FIG. 15 shows an alternative final stage. The attachment parts 31, 32 and anchoring unit 41, 44 are removed from the set of implants by unscrewing fixture screws 6. The upper attachment part 32 is removed from the remainder of the assembly and a final part 150 FIG. 15 is formed which has the shape of the set of parts 31, 41, 44, 48. This new, final, part 150 is secured to upper attachment part 32 and then placed upon the set of implants 5 and secured to the implants 5 by reaffixing screws 6. This alternative scheme has an advantage of creating a final part 150 which lacks any gaps between parts. This can provide a much better sealing against the gum. The shape of the final part 150 is determined by transferring the final implant positions after healing to the design environment, e.g. either directly via scanning or indirectly by first transferring them to a working model e.g. a gypsum cast, which is scanned afterwards. Given the known position of the implants and the known dimensions of the upper part of the attachment the design can be performed accurately.

The invention claimed is:

1. A dental attachment assembly configured in a way such that the dental attachment assembly is mountable to an anchorage unit of a dental implant, the dental attachment assembly comprising:

a first attachment part and a second attachment part configured in a way such that the first attachment part and the second attachment part form an aperture for accommodating a portion of at least one anchorage unit, wherein the aperture defines boundary walls on the first and second attachment which are configured in a way such that the boundary walls form a jaw clampable against the portion of the at least one anchorage unit, wherein the aperture is larger than the portion of the at least one anchorage unit and configured in a way such that a position of the dental attachment assembly is adjustable with respect to the at least one anchorage unit; and a removable dental implant drilling template for use at a treatment site configured in a way such that the removable dental implant drilling template can fit a dental implant, wherein the dental implant drilling template comprises a hole which defines a position for the dental implant and a recess located on a side of the template facing the treatment site, wherein the recess is configured in a way such that the recess accommodates one of said attachment parts of said dental attachment assembly.

2. A dental attachment unit comprising:

at least one dental implant implanted at a treatment site;

at least one anchorage unit configured in a way such that the at least one anchorage unit fits on the at least one dental implant; and a dental attachment assembly according to claim 1 configured in a way such that the dental attachment assembly is mountable to the at least one anchorage unit.

3. The dental attachment unit according to claim 2, wherein said aperture defined by the first attachment part and the second attachment part does not have a greater size in any dimension besides laterally, thereby enabling adjustment in a lateral direction.

4. The dental attachment unit according to claim 2, wherein at least a radially outermost region of the aperture has a height which is greater than the portion of the at least one anchorage unit to thereby permit adjustment in an angular direction.

5. The dental attachment unit according to claim 2, wherein the aperture has a central shaft connecting an upper face of the first attachment part and lower face of the second attachment part with the aperture for permitting access to the at least one dental implant.

6. The dental attachment unit according to claim 2, wherein the anchorage unit has a radially extending flange against which, in use, the attachment parts can clamp.

7. The dental attachment unit according to claim 2, further comprising at least one fixing element arranged to secure the first and second attachment parts together.

8. The dental attachment unit according to claim 2, wherein the at least one anchorage unit comprises a first anchorage element configured to fit to the at least one dental implant and a second anchorage element configured to fit to the first anchorage element, the first and second anchorage elements being configured, in use, to be secured with respect to one another within a range of different longitudinal displacements.

9. The dental attachment unit according to claim 8, wherein the second anchorage element comprises a radially extending flange against which, in use, the first and second attachment parts can clamp.

10. The dental attachment unit according to claim 8, wherein the second anchorage element is configured to fit within the first anchorage element.

11. The dental attachment unit according to claim 2, wherein the at least one anchorage unit comprises a first anchorage element configured to fit to the at least one dental implant and a second anchorage element configured to fit around an outer surface of the first anchorage element.

12. The dental attachment unit according to claim 8, wherein the first anchorage element is configured in a way such that the first anchorage element is connected to the second anchorage element by a rotatable connection.

13. The dental attachment unit according to claim 12, wherein the first anchorage element comprises a shaft having a head and the second anchorage element comprises a socket for receiving the head and permitting, in use, rotation of the second anchorage element with respect to the first anchorage element.

14. The dental attachment unit according to claim 8, wherein the second anchorage unit comprises a head with a radially extending flange.

15. The dental attachment unit according to claim 14, wherein the head has a convex upper surface.

16. The dental attachment unit according to claim 8, further comprising a third anchorage element to which, in use, the second attachment part can clamp, the second anchorage element being rotatable, in use, with respect to the third anchorage element.

17. The dental attachment unit according to claim 16, wherein the third anchorage element is an annular element having a concave upper surface and the second anchorage element has a head with a convex lower surface, the head of the second anchorage element fitting within the third anchorage element.

18. The dental attachment unit according to claim 2, wherein the at least one anchorage unit comprises a channel for receiving a fixing element for engaging with a connection part of the at least one dental implant.

19. The dental attachment unit according to claim 2, further comprising a seal for fitting around the anchorage unit and for sealing between the anchorage unit and one of the attachment parts.

20. The dental attachment unit according to claim 2, wherein an interface between the first attachment part and the second attachment part is substantially parallel to a longitudinal axis of the attachment.

21. The dental attachment unit according to claim 1, wherein the hole has a diameter sufficient to accommodate the implant and an anchorage element for fitting to an implant.

22. A method of fitting a dental attachment to a dental implant at a treatment site comprising:

fitting an anchorage unit to at least one dental implant at least one treatment site;

arranging a first attachment part and a second attachment part of said dental attachment around the anchorage unit, wherein the first and second attachment parts are configured in a way such that the first and second attachment parts form an aperture for accommodating a portion of the anchorage unit, wherein the aperture defines boundary walls on the first and second attachment parts which are configured in a way such that the boundary walls form a jaw that is configured to clamp against the portion of the anchorage unit;

adjusting the position of the dental attachment relative to the anchorage unit, wherein said aperture has a greater size than the portion of the anchorage unit to allow said adjustment with the jaws clamped against said portion of the anchorage unit; and clamping the first and second attachment parts around the anchorage unit to fix the position of the dental attachment and the anchorage unit relative to one another.

23. The method of fitting a dental attachment according to claim 22, further comprising the step of replacing the first attachment part and anchorage unit with a single part which matches the relative positions of said first attachment part and said anchorage unit which achieved the desired fit.

24. The method according to claim 22, further fitting a removable dental implant drilling template for use at a treatment site where the dental implant is to be fitted, wherein the template comprises a hole which defines a position for the dental implant, and a recess located on a side of the template facing the treatment site, wherein the recess is configured in a way such that the recess accommodates one of the attachment parts of said dental attachment assembly.

25. The dental attachment assembly according to claim 1, wherein the boundary wall of the second attachment is inclined allowing rotation of the portion of the at least one anchorage unit.

26. The method according to claim 22, wherein the boundary wall of the second attachment is inclined to allow a rotation of the portion of the anchorage unit.

* * * * *